(12) United States Patent
Soeberdt et al.

(10) Patent No.: US 10,952,945 B2
(45) Date of Patent: Mar. 23, 2021

(54) FORMULATIONS CONTAINING AN EXTRACT OF ECHINACEA AND LINOLEIC ACID DERIVATIVES

(71) Applicant: DR. AUGUST WOLFF GMBH & CO. KG ARZNEIMITTEL, Bielefeld (DE)

(72) Inventors: Michael Soeberdt, Bielefeld (DE); Christoph Abels, Bielefeld (DE); Ulrich Knie, Bielefeld (DE)

(73) Assignee: Dr. August Wolff GMBH and Co. KG Arzneimittel

( * ) Notice: Subject to any disclaimer, the term of this patent is extended or adjusted under 35 U.S.C. 154(b) by 291 days.

(21) Appl. No.: 15/755,649

(22) PCT Filed: Aug. 31, 2016

(86) PCT No.: PCT/EP2016/070438
§ 371 (c)(1),
(2) Date: Feb. 27, 2018

(87) PCT Pub. No.: WO2017/037075
PCT Pub. Date: Mar. 9, 2017

(65) Prior Publication Data
US 2020/0230189 A1 Jul. 23, 2020

(30) Foreign Application Priority Data
Aug. 31, 2015 (DE) .................... 10 2015 011 132.9

(51) Int. Cl.
| | |
|---|---|
| *A61K 36/00* | (2006.01) |
| *A61K 8/37* | (2006.01) |
| *A61K 8/9789* | (2017.01) |
| *A61P 17/04* | (2006.01) |
| *A61K 8/36* | (2006.01) |
| *A61K 31/201* | (2006.01) |
| *A61K 36/28* | (2006.01) |
| *A61Q 19/00* | (2006.01) |

(52) U.S. Cl.
CPC .............. *A61K 8/375* (2013.01); *A61K 8/361* (2013.01); *A61K 8/9789* (2017.08); *A61K 31/201* (2013.01); *A61K 36/28* (2013.01); *A61P 17/04* (2018.01); *A61Q 19/00* (2013.01)

(58) Field of Classification Search
None
See application file for complete search history.

(56) References Cited

U.S. PATENT DOCUMENTS

2009/0197974 A1    8/2009  Khaleeq
2009/0325857 A1*  12/2009  Beumer .................. A61K 8/49
                                                                  514/1.1

FOREIGN PATENT DOCUMENTS

| JP | 11092339 A | * | 4/1999 |
| JP | 2001098263 A | * | 4/2001 |
| RU | 2395273 C1 | * | 7/2010 |
| WO | 2012 013 551 | | 2/2012 |

OTHER PUBLICATIONS

Sun et al, Supercritical fluid extraction of alkylamides from Echinacea angustifolia. Journal of agricultural and food chemistry, (Jul. 3, 2002) vol. 50, No. 14, pp. 3947-3953 (Year: 2002).*
Ruasian Search Report for Application Serial No. 2018111036.
Russian Office Action for Application Serial No. 2018111036.
"Skin Improvement and Stability of Echinacea Purpurea Dermatological Formulations," International Journal of Cosmetic Science, 2010, vol. 32, pp. 340-346.
"Echinacea Purpurea: Pharmacology, Phytochemistry, and Analysis Methods," Pharmacognosy Reviews, Jan.-Jun. 2015, vol. 9, Issue 17, pp. 63-72.
"Biophysical Properties of Dry Atopic and Normal Skin with Special Reference to Effects of Skin Care Products," Acto Derm Venereol Suppl (Stockh), 1995, vol. 192, Abstract.
"Effect of Topically Applied Lipids on Surfactant-Irritated Skin," Br. J. Dermatol, Feb. 1996, vol. 134(2), Abstract.
Author Unknown, "Echinacea Purpurea, Planta Tota 10% Salbe," https://www.medicaria.de/images/ecommerce/01/62/01627942_1970-01_de_s.pdf, date unknown.
Soeberdt, et al., "Anti-inflammatory Activity of Alkylamides from Echinacea Purpurea in Keratinocytes in vitro and in Mouse Models of Inflammatory Skin Diseases" Journal of Investigative Dermatology, Nature Publishing Group, US, vol. 134, No. Suppl. 1, May 1, 2014.
Notarnicola, et al., "Comparison of Shock Wave Therapy and Nutraceutical Composed of Echacea Angustifolia, Alpha Lipoic Acid, Conjugated Linoleic Acid and Quercetin (perinerv) in Patients with Carpal Tunnel Syndrome," International Journal of Immunopathology and Pharmacology, Sage Publications LTD, GB, vol. 28, No. 2, Jun. 1, 2015.
Holcova, et al., "Effects of an Echinacea Ointment on the Regeneration of Irritated Skin" Kosmetische Medizin 2004, DE, vol. 25, No. 5-6, Jan. 1, 2004.
"Auto-Immunity & Inflammation," Journal of Investigative Dermatology (2014), vol. 134, pp. 514 Abstract.
"Effects of an Echinachea Ointment on the Regeneration of Irritated Skin," Kosmetische Medizin (2004): 25(5) Abstract.

* cited by examiner

*Primary Examiner* — Qiuwen Mi
(74) *Attorney, Agent, or Firm* — Emerson Thomson Bennett, LLC; Daniel A. Thomson

(57) ABSTRACT

The present invention relates to pharmaceutical and cosmetic formulations containing an extract of *Echinacea* and linoleic acid derivatives, particularly emulsions containing an extract of *Echinacea* and linoleic acid derivatives as an active agent combination, and the use of such formulations as medicines, medicinal products and/or cosmetics.

20 Claims, 12 Drawing Sheets

FORMULATIONS CONTAINING AN EXTRACT OF ECHINACEA AND LINOLEIC ACID DERIVATIVES

The present invention relates to pharmaceutical and cosmetic formulations containing an extract of *Echinacea* and linoleic acid derivatives, particularly emulsions containing an extract of *Echinacea* and linoleic acid derivatives as an active agent combination, and the use of such formulations as medicines, medicinal products and/or cosmetics.

RELATED ART

Preparations from the purple coneflower (*Echinacea purpurea* and *Echinacea angustifolia*) are used widely in the treatment of colds and infections of the upper respiratory tract. It is generally accepted that the effect of *Echinacea* is enabled by interactions with the immune system. It has been demonstrated that a certain component of the extracts of *Echinacea*, the anti-inflammatory effect of which has been described previously by other working groups, influences the endogenous cannabinoid system. This component is the alkylamide substance class (Raduner S et al., *J Biol Chem* 2006, 281, 14192-14206). These alkylamides exhibit immunomodulatory activity (Gertsch J, *Planta Med* 2008, 74, 638-650).

Capsaicin is an agonist of the Transient Receptor Potential Vanilloid 1 (TRPV1) which exhibits antinociceptive and antipruritic effects after topical administration. Topical dosage forms of capsaicin are used to treat haemodialysis-induced (Breneman D L, et al. *J Am Acad Dermatol* 1992, 26, 91-94), aquagenic (Lotti T, et al. *J Am Acad Dermatol* 1994, 30, 232-235) and brachioradial (Goodless D R, Eaglestein W H, *J Am Acad Dermatol* 1993, 29, 783-784) pruritus. Other application areas include Notalgia paraesthetica (Leibsohn E, *Cutis* 1992, 49, 335-336) and Prurigo nodularis (Ständer S, Luger T, Metze D, *J Am Acad Dermatol* 2001, 44, 471-478).

Components of *Echinacea purpurea* were described as tyrosinase inhibitors (Jiang L, et al., *J Med Plants Res* 2012, 6, 5317-5321). The activity of tyrosinase is linked to the production of melanin by melanocytes (Kim, Y J, Uyama H, *Cell Mol Life Sci* 2005 62, 1707-23). Thus, the inhibition of tyrosinase may lead to reduced biosynthesis of melanin, which in turn results in less pigmentation of the skin, for example. This may entail cosmetic disadvantages when using preparations which contain a tyrosinase inhibitor such as an *Echinacea* extract, for example, as differences between the pigmentation of treated and untreated skin may occur.

The improvement in skin condition following treatment with a formulation containing an *Echinacea* extract has been described (Yotsawimonwat S, et al., *Int J Cosm Sci* 2010, 32, 340-346). For this, alcoholic extracts from the aboveground plant parts of *Echinacea purpurea* were used. In this context, it was shown that both a cream and a gel formulation containing the alcoholic extract of *Echinacea* improve hydration of the skin in test subjects without damaging the epidermal barrier. However, the shelf life of the preparations was very limited. The cream and the gel could be stored for 2 and 4 months respectively at 4° C. The storability could be increased to 7 months by adding an antioxidant.

Besides the known immunostimulatory and anti-inflammatory effects of extracts of *Echinacea purpurea*, some clinical studies include contentious findings regarding the side effects of preparations which contain *Echinacea* (Manayi A, Varizian M, Saeidnia S, *Pharmacogn Rev* 2015, 9, 63-72). According to these studies, pruritus, erythema and urticaria were among the serious side effects observed during treatment with *Echinacea*.

DEFINITION OF THE OBJECT

The object was to provide an active agent combination having better properties than an extract of *Echinacea* alone. In particular, a composition should be provided which has antipruritic effect. The object further consisted in improving the stability of the formulation in order to enable a commercial application of the composition. A further object of the present invention was to prevent undesirable effects of the extract of *Echinacea*, which have an adverse affect on cosmetic application. In particular, the formation of erythemas following treatment with the extract of *Echinacea* was to be prevented. Particular attention was also be paid to preventing the extract of *Echinacea* from impairing pigment formation in the skin.

These objects are solved with the present application according to the claims. In particular, it was unexpectedly found that the composition according to the invention has excellent antipruritic effect in patients with atopic dermatitis, for example, and at the same time has a long storage life of at least two years at room temperature. With this, commercial marketability becomes very possible. Furthermore, it was found according to the invention that the regeneration of the natural epidermal barrier in test subjects and patients with a compromised epidermal barrier is effectively enhanced. It was also surprising to find that treatment with the formulations according to the invention results in a significant increase of lipids in the skin. Particularly noteworthy in this context is the presence of more of the long-chain ceramide EOS, which is particularly important for the stability of the lipid bilayers in the stratum corneum, because this is where an ω-hydroxy fatty acid in the ceramide base is esterified with linoleic acid. This esterification produces a C36-side chain which extends into the next lipid bilayer. This is why these ceramides are also said to have a "nail function".

One of several factors confirming the antipruritic effect is a surprisingly pronounced activation of the Transient Receptor Potential Vanilloid 1 (TRPV1) when the active agent combination according to the invention is administered. The person skilled in the art also would not have expected the combination of active agents *Echinacea* and linoleic acid/linoleic acid derivatives to prevent that known undesirable effect of *Echinacea* on pigment formation in the skin. The adverse effect on pigment formation observed when *Echinacea* is applied to the skin (reduced pigmentation) does not occur with the combination of active agents *Echinacea* and linoleic acid and/or linoleic acid derivatives. This is confirmed by the tyrosinase activity, which remains surprisingly unaffected when the active agent combination according to the invention is used.

The present invention thus relates to a composition containing a) an extract of *Echinacea* and b) linoleic acid and/or linoleic acid derivatives. The extract of *Echinacea* is preferably a lipophilic extract. The extract of *Echinacea* is particularly preferably an extract which is recovered using supercritical $CO_2$. Preferably according to the invention, the extract also has an alkylamide content between 1 and 50%, preferably between 10 and 40%, and particularly preferably between 15 and 30% (relative to weight). In a preferred embodiment of the invention, the extract is taken from *Echinacea* in the roots (radix) of *Echinacea*, preferably from *Echinacea purpurea* radix.

According to the invention, the linoleic acid derivatives are linoleic acid esters, preferably glycerol triesters. In a preferred embodiment, the linoleic acid derivatives are present in the form of a vegetable oil and/or a vegetable oil extract, preferably in the form of safflower oil.

According to the invention, the composition contains the components a) and b) in the weight ratios 1:1000 to 1:1; preferably 1:50 to 1:10. The composition of the invention further contains preferably 0.001-5 wt % *Echinacea* extract, preferably 0.025-2 wt % *Echinacea* extract, particularly preferably 0.05-1 wt % *Echinacea* extract relative to the weight of the total composition, and 0.001-10 wt % linoleic acid and/or a similar quantity of linoleic acid derivatives corresponding to 0.001-10 wt % linoleic acid, preferably 0.01-5 wt % linoleic acid and/or a similar quantity of linoleic acid derivatives corresponding to 0.01-5 wt % linoleic acid relative to the weight of the total composition in each case.

The composition according to the invention preferably further contains one or more cosmetic and/or pharmaceutical adjuvants. The composition is particularly preferably an emulsion.

According to the invention, the composition is used as a medicine, as a medicinal product or as a cosmetic. As such, it preferably serves to treat pruritus, dry skin and/or irritated skin (e.g., skin reddened after sunburn, abrasions or skin which has been made sore in some other way, etc.), and also inflammatory conditions of the skin, particularly such as atopic dermatitis (neurodermatitis, atopic eczema). In a preferred embodiment, the skin is the scalp.

In the following section, the individual components of the composition according to the invention will be explained in greater detail.

As component a) of the composition, the *Echinacea* extract used according to the invention may be a standard commercial extract of the related art (such as is described in WO 2001/066076 A for example). Suitable sources are *Echinacea purpurea*, *Echinacea angustifolia* and *Echinacea pallida*, wherein the extract may be obtained either from the aboveground part of the plant or from the roots (radix). According to the present invention, *Echinacea purpurea* is preferred, and particularly preferred is an extract of the roots of *Echinacea purpurea*. According to the invention, the extraction may be carried out with organic solvents such as alcohols (e.g., methanol, ethanol), aqueous solutions of alcohols (e.g., methanol, ethanol), alkanes (e.g., pentane, hexane, heptane), chlorinated hydrocarbons (e.g., chloroform, methylene chloride), ketones (e.g., methyl ethyl ketone, acetone), or by extraction with supercritical carbon dioxide ($CO_2$). In this context, lipophilic extracts are preferred. According to the invention, extraction with supercritical carbon dioxide is particularly preferred, because natural spring carbonic acid can be used and the particularly pure extract can be recovered without harsh methods. Moreover, the solvent $CO_2$ can be removed easily and without residue and recycled in a closed circuit system.

The alkylamide content in the extract is preferably in a range between 1 and 50%, preferably between 10 and 40%, and particularly preferably between 15 and 30% (relative to weight). In this context, the alkylamide content can be determined according to known analytical methods. An example of such may be determination of the alkylamide content by mass spectrometry. The alkylamide content may also be determined by chromatography, e.g., HPLC chromatography with reference substances.

The composition according to the invention contains linoleic acid and/or one or more linoleic acid derivative(s) as the second active component b). Linoleic acid is (cis,cis)-octadeca-9,12-dienoic acid, a double unsaturated fatty acid with 18 carbon atoms (18:2). It thus belongs to the group of omega-6 fatty acids. According to the invention, both the free linoleic acid and a linoleic acid derivative may be used. The term derivatives refers to the esters (particularly the mono-, di- and triglycerides of linoleic acid and mono- and diesters of linoleic acid derived from glycol) which exist as free compounds or also in the form of natural oils and fats, and salts of linoleic acid. Preferred alkyl esters of linoleic acid are methyl-, ethyl-, propyl- and isopropyl esters. Linoleic acid occurs naturally, bonded as an ester in many triglycerides (glycerol triesters). According to the invention, therefore, various natural oils and fats that contain linoleic acid esters in significant quantities are suitable for use as sources of linoleic acid. A list of preferred sources in this context may include the vegetable oils such as salicornia oil, evening primrose oil, grape seed oil, safflower oil, poppy seed oil, prickly pear seed oil, hemp oil, soya oil, cottonseed oil, wheatgerm oil, corn oil, sunflower oil, walnut oil, sesame oil, argan oil, pistachio oil, peanut oil, rapeseed oil, rice oil and olive oil. Linoleic acid and linoleic acid derivatives can be extracted from these oils in known manner before use. Alternatively, the natural oils and fats may be used directly in their native form as linoleic acid component b) in the composition according to the invention. Safflower oil is particularly preferred in this context.

The proportions of components a) and b) in the composition are preferably as follows: 0.001-5 wt % *Echinacea* extract, preferably 0.025-2 wt % *Echinacea* extract, particularly preferably 0.05-1 wt % *Echinacea* extract relative to the weight of the total composition, and 0.001-10 wt % linoleic acid and/or a similar quantity of linoleic acid derivatives corresponding to 0.001-10 wt % linoleic acid, preferably 0.01-5 wt % linoleic acid and/or a similar quantity of linoleic acid derivatives corresponding to 0.01-5 wt % linoleic acid, relative to the weight of the total composition in each case. The formulations according to the invention preferably do not contain any extract other than the *Echinacea* extract, particularly no other plant extract. The linoleic acid source (e.g., natural oils and fats such as safflower oil) is not to understood as an extract for the purposes of the invention.

The formulations according to the invention preferably also contain one or more cosmetic or pharmaceutical adjuvants. The formulations according to the invention are preferably present in the form of an emulsion, and in such case particularly preferably as a topical formulation. A cream or body milk is particularly suitable in this case. The adjuvants that can be used according to the invention are therefore the adjuvants which are typically used in these technical areas, particularly the substances which are known to be used in topical formulations. Suitable adjuvants are described for example in WO 2001/066076 A and DE 10 2005 029 387 A1. Two particularly preferred formulations in the form of a cream and a body milk are listed later in the Examples section of the present application.

EXAMPLES

Example 1

Determination of TRPV1 Agonistic Activity.
A) Experimental Method
$2 \times 10^4$ 293 T-VR1 cells (or parentale 293T cells as control) are cultivated in 96-well microtiter plates (Costar, Cambridge, Mass.) in 200 µL Dulbecco's Modified Eagle's Medium (DMEM), which also contains 10% foetal calf serum and 1% antibiotics (penicillin/streptomycin). The cells are incubated for 6 h with the test substances or the controls (capsaicin, TRPV1 agonist (1 µM); capsazepine, TRPV1 antagonist (10 µM); or capsaicin (1 µM) and capsazepine (10 µM)). Then, cell viability is determined.

The cytotoxic effect of the test substances was determined using the MTT (3-[4,5-dimethylthiazol-2-yl]-2,5-diphenyltetrazolium bromide) assay method. For this, 50 µL of a solution of MTT in DMEM (5 mg/mL) were added to each well. These were then incubated in the dark for 4 h at 37° C. The reaction was stopped, the residue was removed and 100 µL DMSO were added to each well. Incubation continued for 10 min with gentle shaking. Then the absorption at 550 nm was measured with a TECAN GENios Pro Plate Reader (Tecan Group Ltd., Switzerland). The results were presented as a percentage of the control (vehicle solution, 100%). The determination was performed in triplicate.

B) Effects of test substances on the activation of TRPV1

Figure 1:
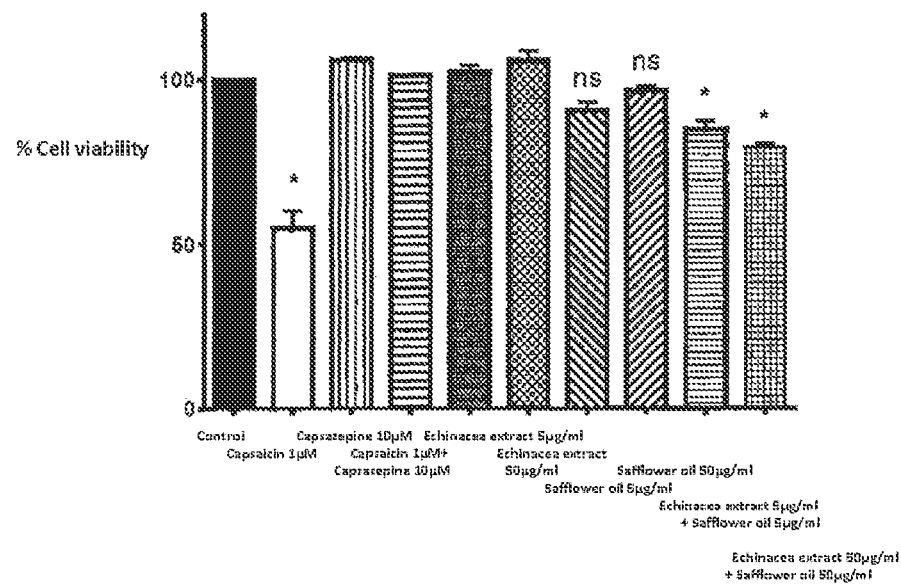
FIG. 1 is a diagram showing the effects of *Echinacea* extract, safflower oil and a mixture of *Echinacea* extract and safflower oil compared with the control substances capsaicin and capsazepine on the activation of TRPV1.

FIG. 1 shows the effects of *Echinacea* extract, safflower oil and a mixture of *Echinacea*-extract and safflower oil on the activation of TRPV1 compared with the control substances capsaicin and capsazepine.

Cell viability was reduced to 54.9% by the treatment with the positive control, the TRPV1 agonist capsaicin. The TRPV1 antagonist capsazepine alone showed no effect (106.1% cell viability). The effect of capsaicin was blocked with capsazepine (101.3% cell viability), proving that the cytotoxic effect is mediated via TRPV1. No cytotoxic effect was observed in the cells that were treated with the extract of *Echinacea* (5 µg/mL or 50 µg/mL) (102.3 and 106.0% cell viability). Only a small, insignificant cytotoxic effect was observed in the cells that were treated with safflower oil (5 µg/mL or 50 µg/mL) (90.5 and 96.5%). Surprisingly, the cells treated with a mixture of the extract of *Echinacea* and safflower oil (5 µg/mL respectively or 50 µg/mL respectively) showed a clear, significant cytotoxic effect. With 85.0% cell viability, the magnitude of the effect was greater than for safflower oil alone, even at the lower concentration. In fact, at the higher concentration cell viability of only 79.3% was determined.

Surprisingly, these results showed that the mixture of the *Echinacea* extract and safflower oil has a synergistic effect on the activation of TRPV1, which occurs even at lower concentrations and considerably surpasses the effects of the individual substances.

Figure 2:
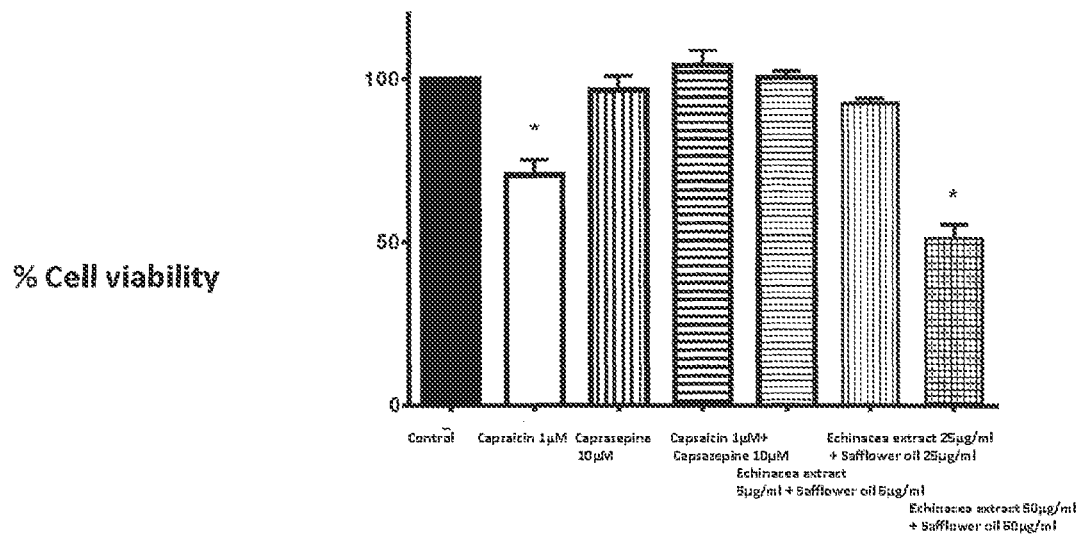
FIG. 2 is a diagram showing the dose response curve for the effects of a mixture of *Echinacea* extract and safflower oil compared with the control substances capsaicin and capsazepine on the activation of TRPV1.

FIG. 2 shows the dose response curve for the effects of a mixture of *Echinacea* extract and safflower oil on the activation of TRPV1 compared with the control substances capsaicin and capsazepine.

In this experiment, the agonistic activity of the positive control capsaicin was found to be slightly lower (70.6% cell viability).

As in the previous experiment, the effect of capsaicin could again be inhibited with the TRPV1 antagonist capsazepine (104.4% cell viability). The mixture *Echinacea* extract and safflower oil exhibited agonistic effects which varied as a function of the dose. For the highest concentration (50 µg/mL in each case), an effect magnitude (51.2% cell viability) exceeding the effect of capsaicin was achieved.

Example 2

Inhibition of Tyrosinase Activity in B16 Melanoma Cells
A) Experimental Method

For the determination of tyrosinase activity, mouse B16 melanoma cells (4A5, ATCC) were cultivated in Dulbecco's Modified Eagle's Medium (DMEM), which also contained 10% foetal calf serum and 1% antibiotics (penicillin/streptomycin). The cells were treated for three days with various concentrations of the test substances. Then, the cells were lysed for 30 min at 4° C. with a lysis buffer (20 mM sodium phosphate, pH 6.8, 1% triton X-100, 1 mM PMSF, 1 mM EDTA), containing a protease inhibitor cocktail. The lysates were centrifuted at 15,000×g for 10 min. The residue was used as the tyrosinase source. The reaction mixture for determination of tyrosinase activity contains 20 mM phosphate buffer, pH 6.8, and 1.25 µM L-Dopa (Sigma-Aldrich). After incubation for 30 min at 37° C., the formation of dopachrome was determined. For this, the absorption at a wavelength of 475 nm was measured in a microtiter plate reader (TriStar LB 941, Berthold Technologies, GmbH & Co. KG). Kojic acid was used as the positive control for the inhibition of tyrosinase activity.

B) Inhibition of Tyrosinase Activity by the Test Substances

Figure 3:
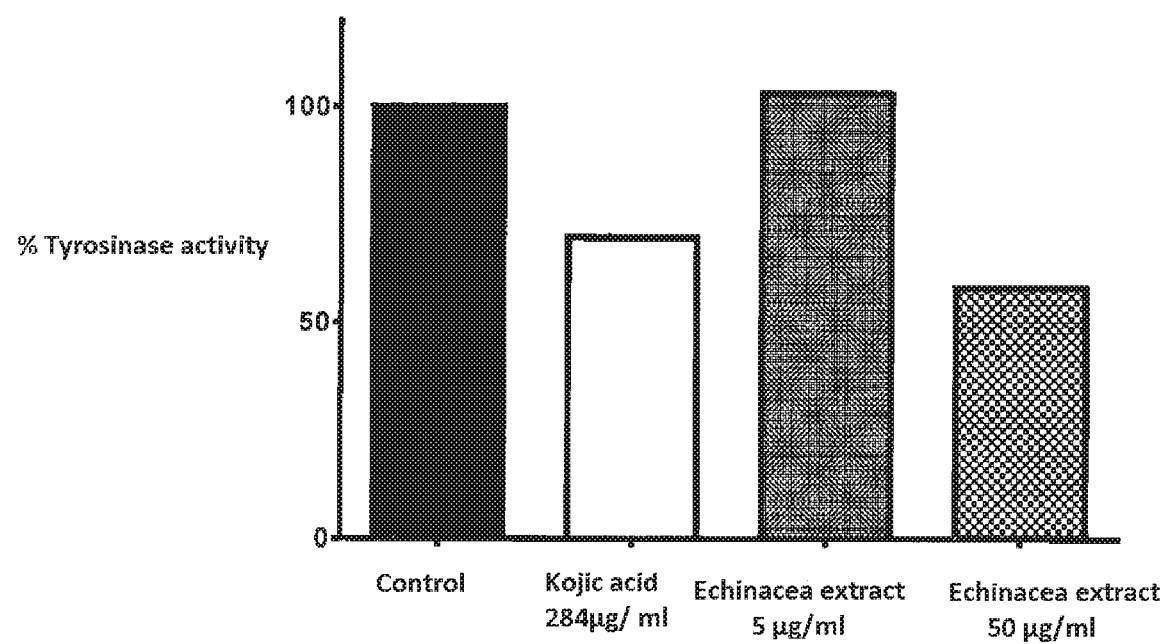
FIG. 3 is a diagram showing the effect of *Echinacea* extract on tyrosinase activity in B16 melanoma cells. Kojic acid is used as the positive control for tyrosinase activity inhibition.

FIG. 3 Shows the Inhibition of Tyrosinase Activity by the Extract of *Echinacea* Compared with Kojic Acid.

For the kojic acid positive control, tyrosinase activity inhibition was determined to be at a level of 30.2%. No inhibition of tyrosinase activity was observed with the *Echinacea* extract in a test concentration of 5 µg/mL. At the higher test concentration of 50 µg/mL, inhibition at a level of 41.8% was determined. Accordingly, the effect was greater than that of the positive control.

Figure 4:
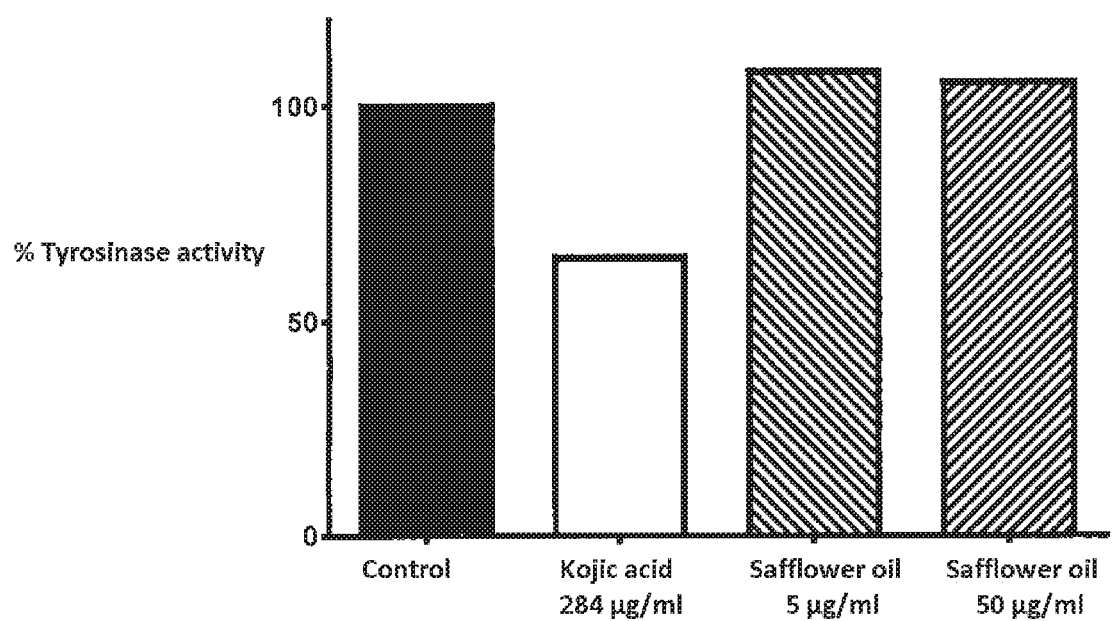
FIG. 4 is a diagram showing the effect of safflower oil on tyrosinase activity in B16 melanoma cells.

FIG. 4 shows the inhibition of tyrosinase activity by safflower oil compared with kojic acid.

Kojic acid as a positive control exhibited tyrosinase activity inhibition at a level of 35.3%. No inhibition of tyrosinase activity was observed with safflower oil at either of the two test concentrations.

Figure 5:
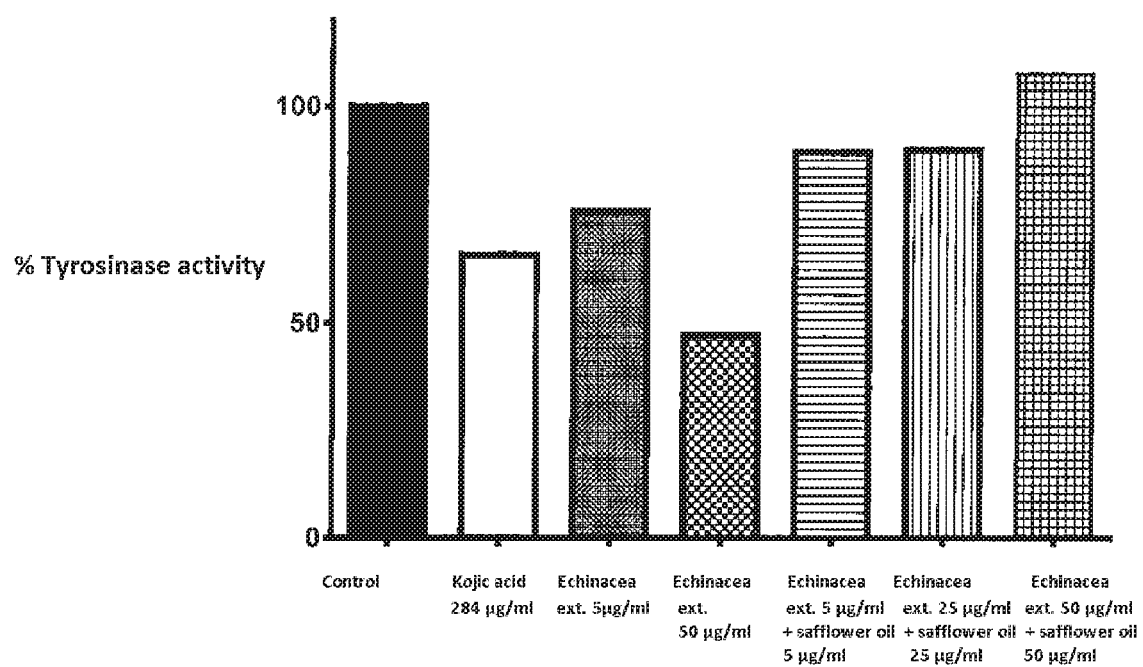
FIG. 5 is a diagram showing the effect of a mixture of *Echinacea* extract and safflower oil on tyrosinase activity in B16 melanoma cells.

FIG. 5 shows the inhibition of tyrosinase activity by the extract of *Echinacea* and a mixture of *Echinacea* extract with safflower oil compared with kojic acid. As in the two preceding experiments, tyrosinase activity inhibition was again observed with kojic acid as the positive control. This inhibition was at a level of 34.3%. For the extract of *Echinacea*, tyrosinase activity inhibition was found to be at levels of 24.3 and 52.8% for the two concentrations (5 µg/mL and 50 µg/mL). This confirmed the results of the first experiment. Surprisingly, no tyrosinase activity inhibition was observed for the mixtures of *Echinacea* extract and safflower oil. This was 89.4-107.5% of the control.

These results show that by adding safflower oil to the extract of *Echinacea* it is possible to cancel the inhibition of tyrosinase activity with a constant test concentration of the *Echinacea* extract.

Example 3

Regeneration of the Epidermal Barrier Following Treatment with Sodium Dodecyl Sulphate (SDS).

The purpose of the study was to determine the influence of a composition according to the invention on the regeneration of impaired epidermal barrier function after treatment for twenty-four hours with sodium dodecyl sulphate (Patch Test).

A) Study Design

The study was a randomised, double-blind study with intra-individual comparison on dermatologically healthy test subjects (n=23).

B) Performance of the Study

On Day 1 of the study, a solution of 0.5% SDS was applied occlusively to the volar forearm using patches (Finn Chambers®, extra large, on Scanpore®) for 24 hours. After removal of the patch on Day 2, the damage to the epidermal barrier was measured. On Days 2 to 11, the test area was treated twice daily with the test products. Instrument measurements were conducted on Days 3, 5 and 8.

A cream with *Echinacea* extract (0.5 wt %) and linoleic acid derivatives (corresponding to the example cream described below) according to the invention and a placebo cream were used as the test products. The test products were applied twice daily over an area of 5 cm×6 cm in each case. 2 mg/cm$^2$ of the test substances were applied in each case.

The test subjects were male and female. They were aged between 18 and 55 years.

Determination of transepidermal water loss:

Transepidermal water loss (TEWL) is a non-invasive method for determining the integrity of the epidermal barrier function of the stratum corneum and is considered to be a sensitive parameter for surfactant-induced skin irritation. TEWL was determined with a DermaLab (Cortex, Denmark) (triple determination). The measuring probe was placed on the skin surface to be measured for 40 s for each measurement. The first 20 s served to equilibrate the system. The values from the second 20 s were averaged and evaluated as a measurement value. Values for TEWL were expressed with the unit g/m$^2$h. The usual range for normal, non-irritated skin is between 3 and 9 g/m$^2$h. Mildly irritated skin with an impaired epidermal barrier typically returns values between 10 and 18 g/m$^2$h depending on the test subjects' starting values. Heavily irritated skin with a significantly impaired epidermal barrier prompts values >25 g/m$^2$h. Thus, a rise in TEWL values is indicative of impaired function of the epidermal barrier.

C) Effects of the Test Products on the Epidermal Barrier

Figure 6:
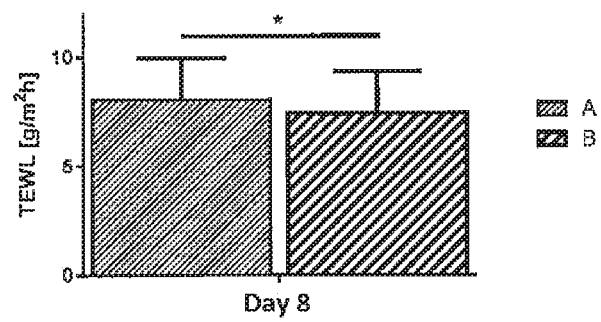
FIG. 6 is a diagram showing the effect of a cream with *Echinacea* extract and linoleic acid derivatives according to the invention on transepidermal water loss compared with a placebo cream (A: Placebo cream; B: Cream with *Echinacea* and linoleic acid derivatives).

FIG. 6 shows the effect of the cream with *Echinacea* extract and linoleic acid derivatives according to the invention on transepidermal water loss compared with the placebo cream.

The application of both test products resulted in a marked reduction of transepidermal water loss, which was >20 g/m$^2$h on Day 2. Surprisingly, the results showed that the effect of the cream with *Echinacea* extract and linoleic acid derivatives according to the invention on the reduction of transepidermal water loss is significantly greater than with the placebo cream on Day 8.

Example 4

Study on Patients with Atopic Dermatitis (3 Months)

A) Study Design

The study was a randomised, double-blind study with comparison product control and with intra-individual comparison.

B) Performance of the Study

The cream with *Echinacea* extract (0.5 wt %) and linoleic acid derivatives (corresponding to the example cream described below) according to the invention and a conventional cream (water-in-oil cream, fat content approx. 55%, approx. 2.5% plant extract containing betulin) as the comparison preparation were used as the test preparations. The products were applied twice daily. The products were applied to contralateral skin surfaces over an area of 1600 cm$^2$ (40×40 cm, approx. 9% of the surface of an adult man) for each product in each case. The cubital fossa and the entire arm or alternatively the popliteal fossa and the half of the leg above and below the knees or the half of one side of the upper body were selected as application sites. The products were applied for about 3 months (85 days). The application quantity was 1.5 g per product application. Pruritus was evaluated by the investigating physician and the patient gave a subjective evaluation of the sensation of dryness on Days 1 (Start), 29 (1 month), 57 (2 months) and 85 (3 months).

C) Reduction of Sensation of Skin Dryness and Pruritus Following Treatment with the Cream with *Echinacea* Extract and Linoleic Acid Derivatives According to the Invention (n=46-48)

Figure 7:
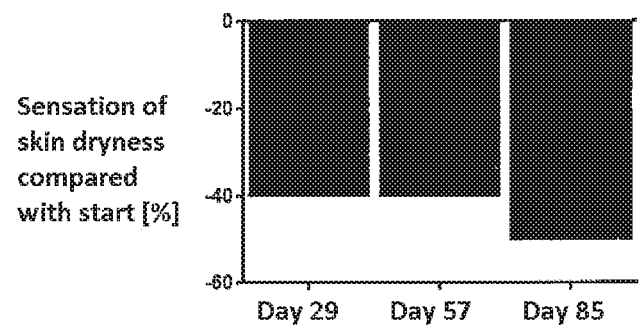
FIG. 7 is a diagram showing the reduction of the feeling of skin dryness following treatment with a cream with *Echinacea* extract and linoleic acid derivatives according to the invention.

FIG. 7 shows the reduction over time of the sensation of skin dryness following treatment with the cream with *Echinacea* extract and linoleic acid derivatives according to the invention.

Following treatment with the cream with *Echinacea* extract and linoleic acid derivatives according to the invention, the sensation of skin dryness was reduced by 40% on Day 29 compared with the start of treatment. On Days 57 and 85, the reduction was 40% and 50% respectively. The reduction of the sensation of skin dryness on Day 85 was significantly greater than with the comparison preparation (−35%).

Figure 8:
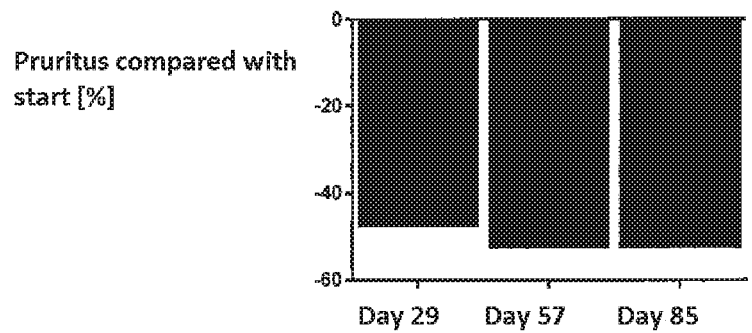
FIG. 8 is a diagram showing the reduction of pruritus following treatment with a cream with *Echinacea* extract and linoleic acid derivatives according to the invention.

FIG. 8 shows the reduction over time of pruritus following treatment with the cream with *Echinacea* extract and linoleic acid derivatives according to the invention.

Following treatment with the cream with *Echinacea* extract and linoleic acid derivatives according to the invention, pruritus was reduced by 47.6% on Day 29 compared with the start of treatment. On Days 57 and 85, pruritus reduction was 52.4%. The reduction of the sensation of skin dryness on Days 57 and 85 was significantly greater than with the comparison preparation (−33.3% in each case).

Example 5

14 d Study in Patients with Atopic Dermatitis

A) Study Design

The study with conducted with an intra-individual, double-blind comparison.

B) Performance of the Study

The study was conducted on test subjects with atopic diathesis (aged from 18 to 70 years (22 female, 3 male, local SCORAD between 1 and 15)). The cream with *Echinacea* extract (0.5 wt %) and linoleic acid derivatives according to the invention and the body milk containing *Echinacea* extract (0.1 wt %) and linoleic acid derivatives according to the invention (corresponding to the example cream and example body milk described below) were used as the test preparations. The products were applied twice daily for 14 days.

Skin moisture was determined on Day 1 and Day 15 by corneometry. The examination of the epidermal skin barrier was carried out directly without invasive sampling by Microscopy Services Dahnhardt (Flintbek, Germany) using the Lipbarvis® (Lipid Barrier Visualisation, LBV) analytical method. For this purposes, skin samples of three to five cell layers were taken by means of a particularly gentle adhesive/carrier system.

Before/After comparisons of the lipid lamellas (LBV-TEM): The samples were prepared and examined with a transmission electron microscope. A special software program determined the length of the lipid lamellas and correlated this with the intercellular space. The number of lipid lamellas enables very accurate conclusions to be drawn regarding the effectiveness of the active agent applied.

Determination of Skin Lipids (LBV-LIP):

The important skin lipids such as cholesterol, fatty acids, ceramides EOS, NP and NH were determined quantitatively by HPTLC analysis (High Performance Thin Layer Chromatography) of the skin sample for total and individual lipids.

C) Increase of Lipid Lamellas Following Treatment with the Cream with *Echinacea* Extract and Linoleic Acid Derivatives According to the Invention or the Body Milk Containing *Echinacea* Extract and Linoleic Acid Derivatives According to the Invention, Increased Synthesis of the Skin's Own Lipids and Increase in Skin Moisture (n=20)

Figure 9:
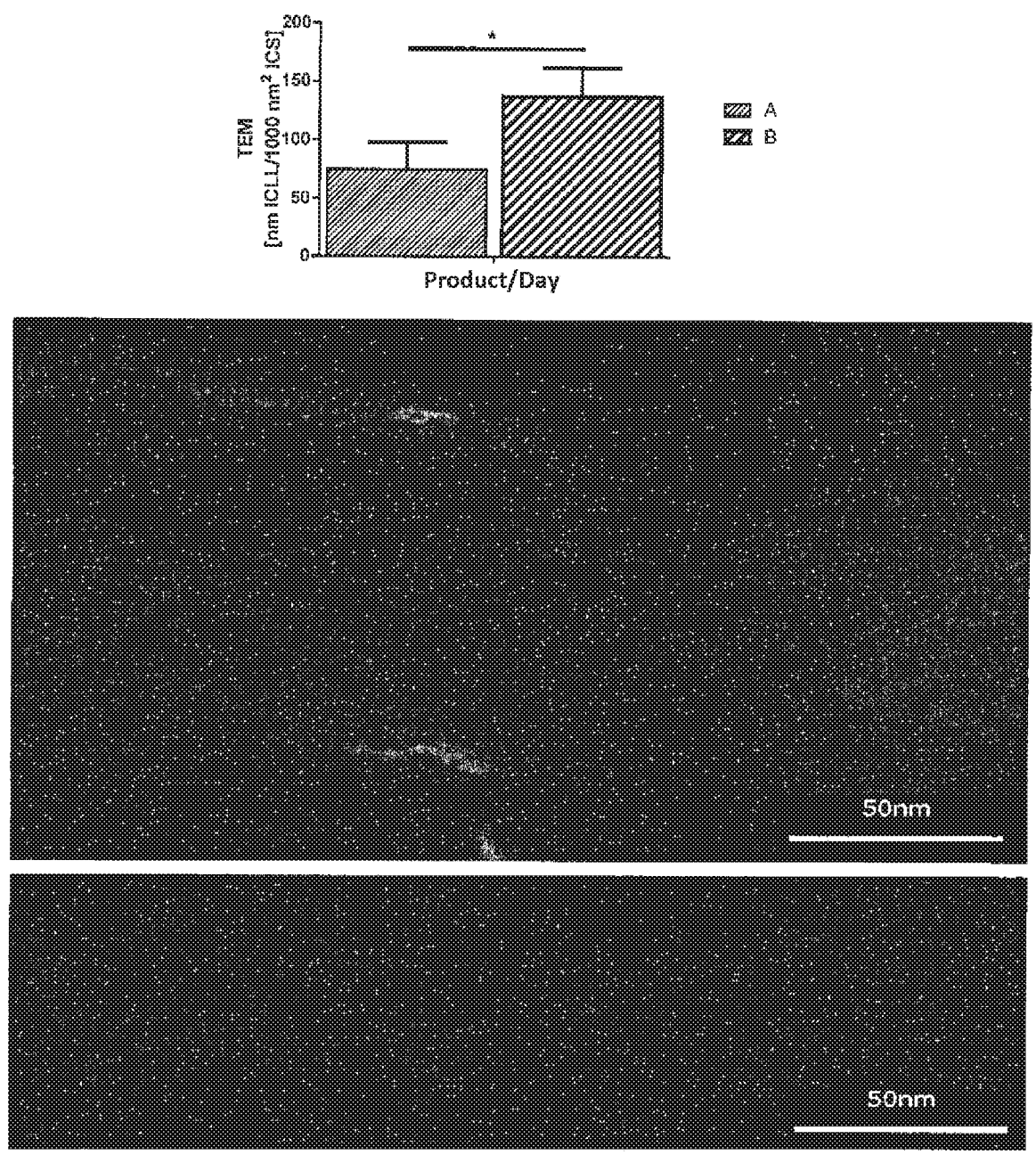
FIG. 9 is a diagram showing a before/after comparison of the lipid lamellas (LBV-TEM) following treatment with a cream according to the invention containing *Echinacea* extract and linoleic acid derivatives (top graphic with quantitative evaluation, A: Cream with *Echinacea* and linoleic acid derivatives/Day 1; B: Cream with *Echinacea* and linoleic acid derivatives/Day 15, representative Transmission Electron Microscope (TEM) image Day 1, middle, TEM image Day 15, bottom).

FIGS. 9 (cream) and 16 (body milk) show the Before/After comparison of lipid lamellas (LBV-TEM) following treatment with a product containing *Echinacea* extract and linoleic acid derivatives.

In both cases, a significant increase in the lipid lamella count was found according to the invention.

Figure 10:
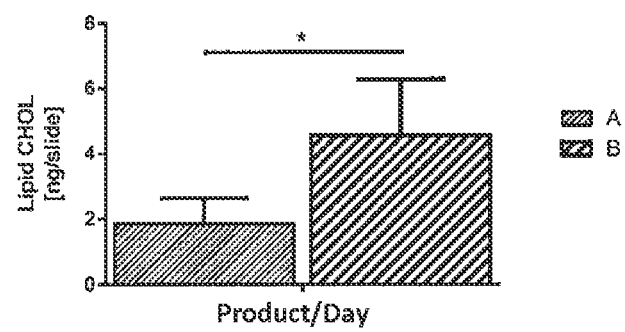
FIG. 10 is a diagram showing a before/after comparison of the cholesterol content following treatment with a cream according to the invention containing *Echinacea* extract and linoleic acid derivatives (A: Cream with *Echinacea* and linoleic acid derivativese/Day 1; B: Cream with *Echinacea* and linoleic acid derivativese/Day 15).

FIGS. 10 (cream) and 17 (body milk) show the Before/After comparison of cholesterol content following treatment with a product containing *Echinacea* extract and linoleic acid derivatives.

An increase in the cholesterol content was found for both products. The difference was particularly significant for the cream with *Echinacea* extract and linoleic acid derivatives according to the invention.

Figure 11:
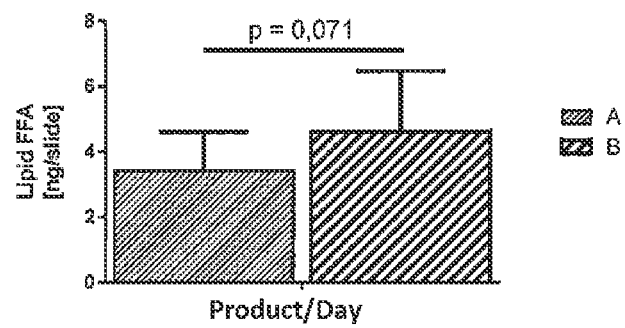
FIG. 11 is a diagram showing a before/after comparison of the free fatty acid (FFA) content following treatment with a cream according to the invention containing *Echinacea* extract and linoleic acid derivatives (A: Cream with *Echinacea* and linoleic acid derivatives/Day 1; B: Cream with *Echinacea* and linoleic acid derivatives/Day 15).

FIGS. 11 (cream) and 18 (body milk) show the Before/After comparison of the free fatty acid (FFA) content following treatment with a product containing *Echinacea* extract and linoleic acid derivatives.

For both products, a significant increase in the free fatty acid content according to the invention was found.

Figure 12:
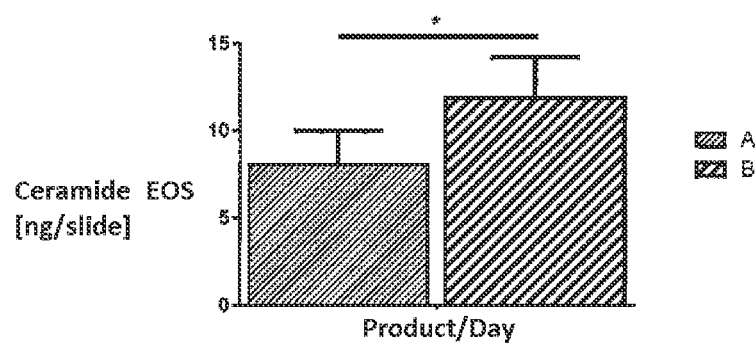
FIG. 12 is a diagram showing a before/after comparison of the ceramide EOS content following treatment with a cream according to the invention containing *Echinacea* extract and linoleic acid derivatives (A: Cream with *Echinacea* and linoleic acid derivatives/Day 1; B: Cream with *Echinacea* and linoleic acid derivatives/Day 15).

FIGS. 12 (cream) and 19 (body milk) show the Before/After comparison of ceramide EOS content following treatment with a product containing *Echinacea* extract and linoleic acid derivatives.

An increase in the ceramide EOS content was found for both products according to the invention. The difference was particularly significant for the cream with *Echinacea* extract and linoleic acid derivatives according to the invention.

Figure 13:
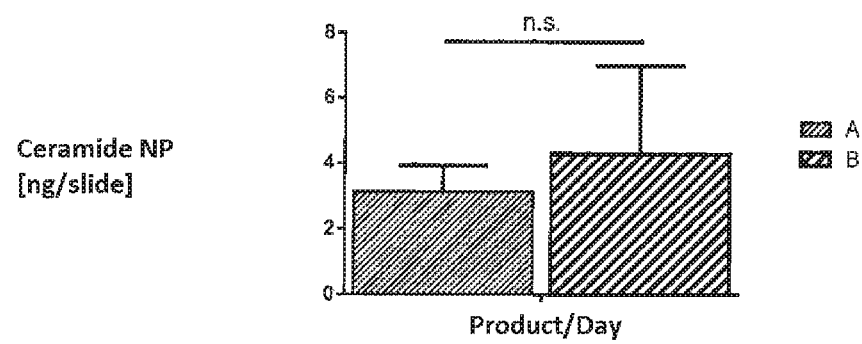
FIG. 13 is a diagram showing a before/after comparison of the ceramide NP content following treatment with a cream according to the invention containing *Echinacea* extract and linoleic acid derivatives (A: Cream with *Echinacea* and linoleic acid derivatives/Day 1; B: Cream with *Echinacea* and linoleic acid derivatives/Day 15).

FIGS. 13 (cream) and 20 (body milk) show the Before/After comparison of ceramide NP content following treatment with a product containing *Echinacea* extract and linoleic acid derivatives.

An increase in the ceramide NP content was found for both products according to the invention. The difference was particularly significant for the body milk with *Echinacea* extract and linoleic acid derivatives according to the invention.

Figure 14:
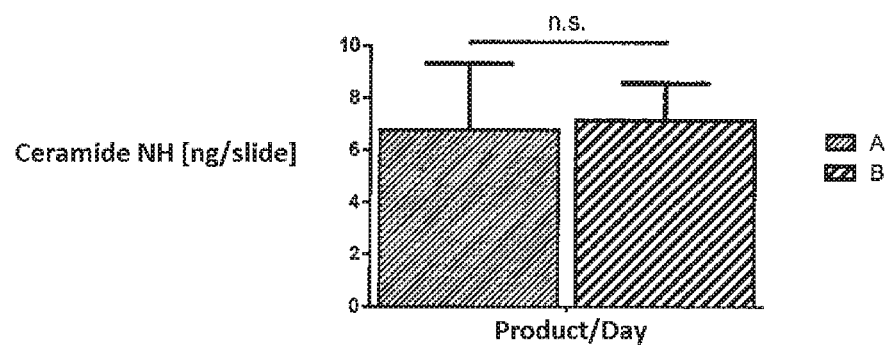
FIG. 14 is a diagram showing a before/after comparison of the ceramide NH content following treatment with a cream according to the invention containing *Echinacea* extract and linoleic acid derivatives (A: Cream with *Echinacea* and linoleic acid derivatives/Day 1; B: Cream with *Echinacea* and linoleic acid derivatives/Day 15).

FIGS. 14 (cream) and 21 (body milk) show the Before/After comparison of ceramide NH content following treatment with a product containing *Echinacea* extract and linoleic acid derivatives.

An increase in the ceramide NH content was found for both products according to the invention. The difference was particularly significant for the body milk with *Echinacea* extract and linoleic acid derivatives according to the invention.

Figure 15:
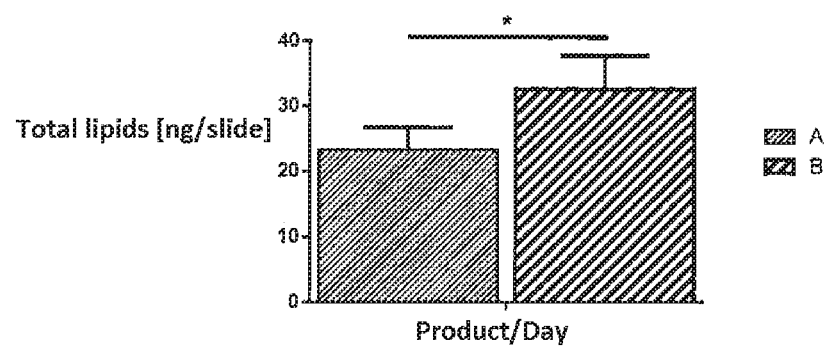
FIG. 15 is a diagram showing a before/after comparison of the total lipid content following treatment with a cream according to the invention containing *Echinacea* extract and linoleic acid derivatives (A: Cream with *Echinacea* and linoleic acid derivatives/Day 1; B: Cream with *Echinacea* and linoleic acid derivatives/Day 15).
Figure 16:
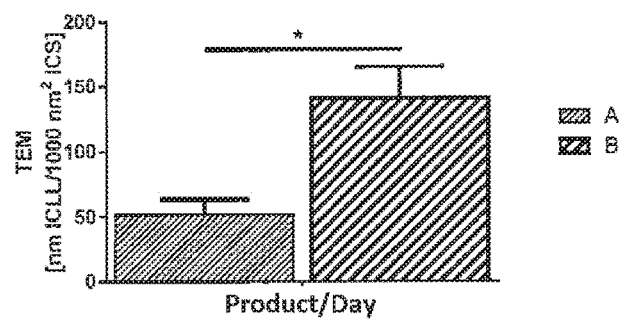
FIG. 16 is a diagram showing a before/after comparison of the lipid lamellas (LBV-TEM) following treatment with a body milk according to the invention containing *Echinacea* extract and linoleic acid derivatives (top graphic with quantitative evaluation, A: Body milk with *Echinacea* and linoleic acid derivatives/Day 1; B: Body milk with *Echinacea* and linoleic acid derivatives/Day 15, representative Transmission Electron Microscope (TEM) image Day 1, middle, TEM image Day 15, bottom).
Figure 16:
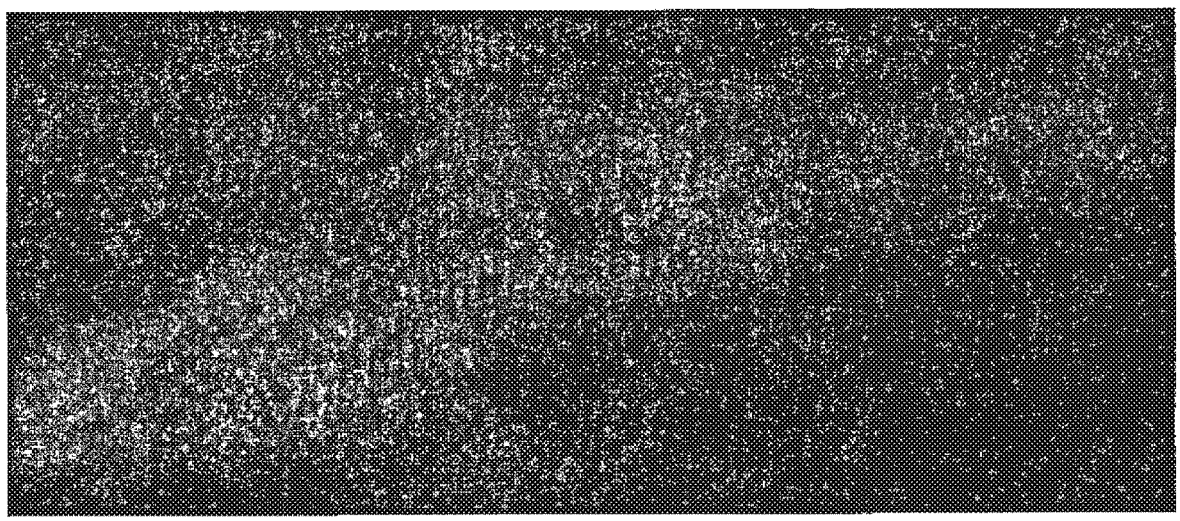
Figure 16:
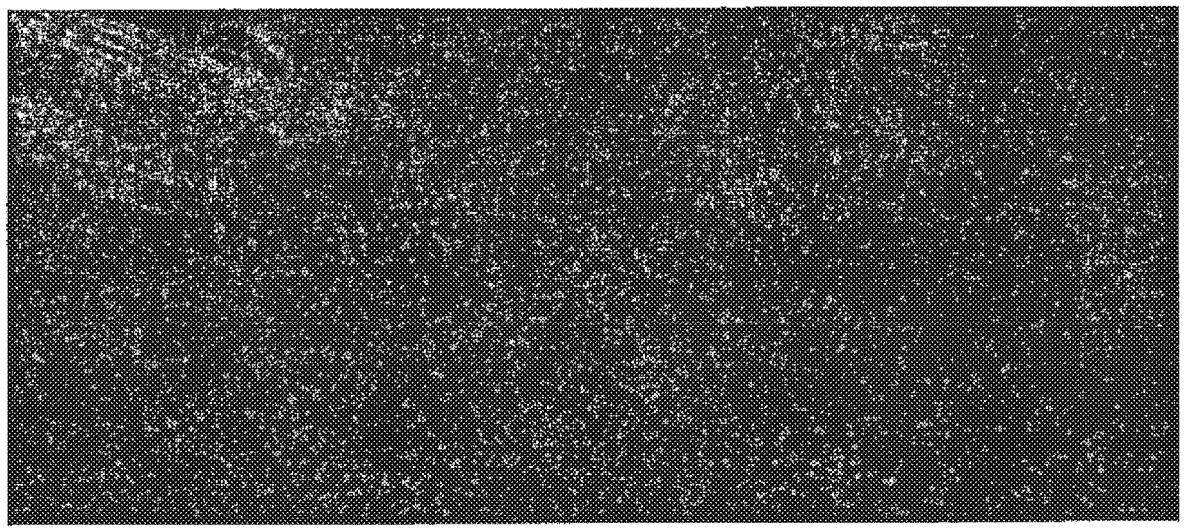
Figure 17:
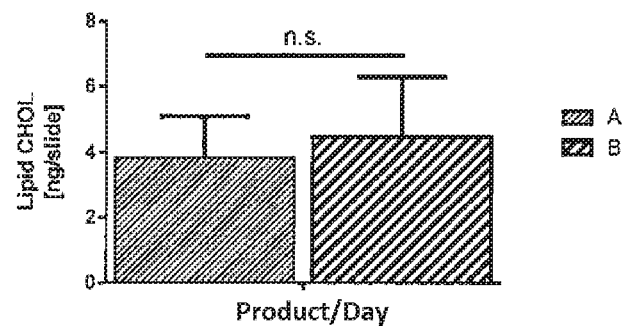
FIG. 17 is a diagram showing a before/after comparison of the cholesterol content following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).
Figure 18:
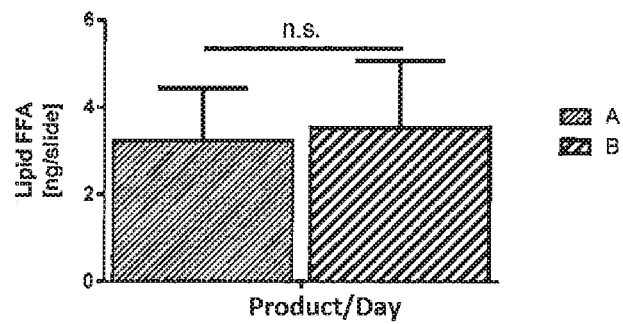
FIG. 18 is a diagram showing a before/after comparison of the free fatty acids (FFA) content following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).
Figure 19:
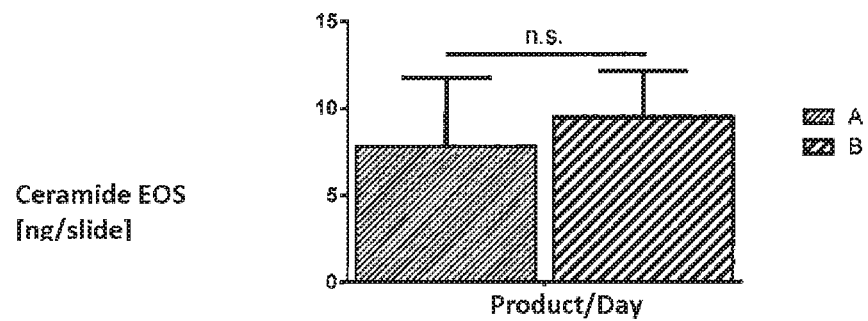
FIG. 19 is a diagram showing a before/after comparison of the ceramide EOS content following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).
Figure 20:
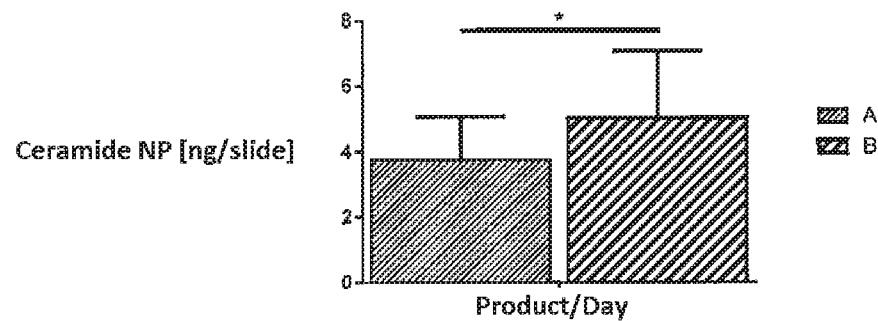
FIG. 20 is a diagram showing a before/after comparison of the ceramide NP content following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).
Figure 21:
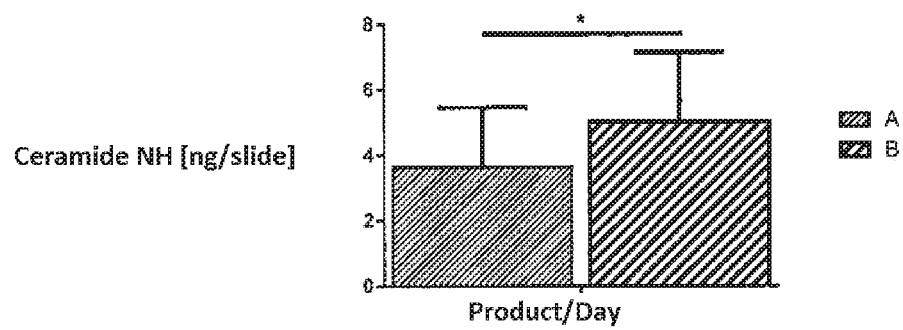
FIG. 21 is a diagram showing a before/after comparison of the ceramide NH content following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).
Figure 22:
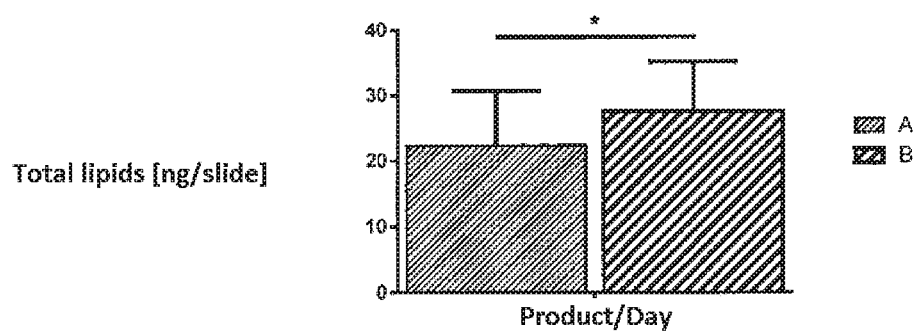
FIG. 22 is a diagram showing a before/after comparison of the total lipid content following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).

FIGS. 15 (cream) and 22 (body milk) show the Before/After comparison of total lipid content following treatment with a product containing *Echinacea* extract and linoleic acid derivatives.

An increase in the total lipid content was found for both products according to the invention. The difference was significant for both groups.

Figure 23:
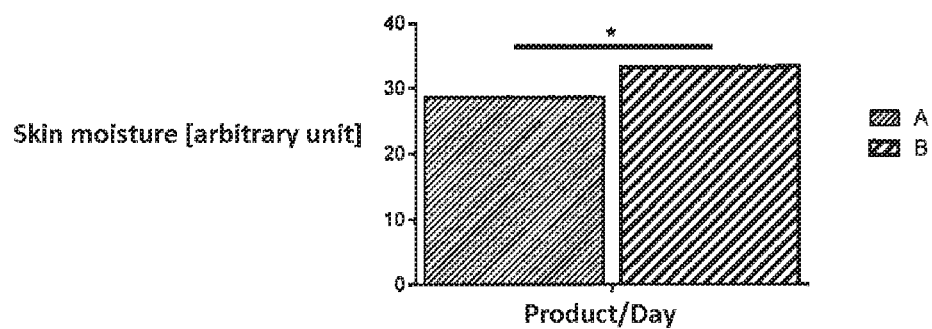
FIG. 23 is a diagram showing a before/after comparison of skin moisture following treatment with a cream according to the invention containing *Echinacea* extract and linoleic acid derivatives (A: Cream with *Echinacea* and linoleic acid derivatives/Day 1; B: Cream with *Echinacea* and linoleic acid derivatives/Day 15).
Figure 24:
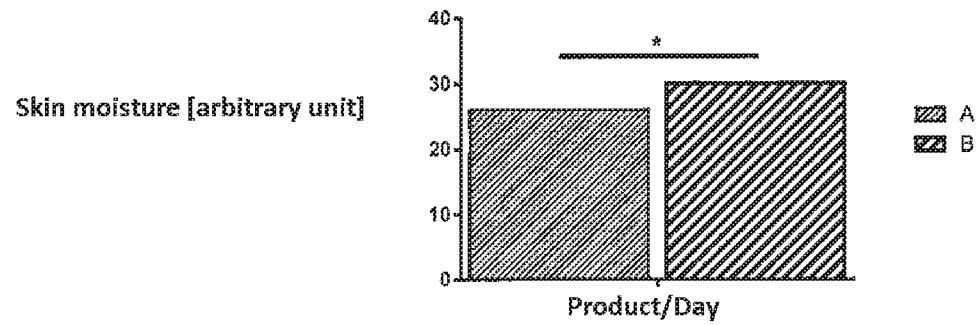
FIG. 24 is a diagram showing a before/after comparison of skin moisture following treatment with a body milk according to the invention containing *Echinacea* extract and linoleic acid derivatives (A: Body milk with *Echinacea* and linoleic acid derivatives/Day 1; B: Body milk with *Echinacea* and linoleic acid derivatives/Day 15).

FIGS. 23 (cream) and 24 (body milk) show the Before/After comparison of skin moisture following treatment with a product containing *Echinacea* extract and linoleic acid derivatives.

Skin moisture was increased significantly following treatment with the cream containing *Echinacea* extract and linoleic acid derivatives according to the invention or the body milk containing *Echinacea* extract and linoleic acid derivatives according to the invention.

Example 6

Clinical Study to Investigate Potential for Irritation and Sensitisation

A) Study Design

The study was a double-blind, randomised, single-centre study with comparison product control.

B) Performance of the Study

The study was conducted with 105 volunteer test subjects (aged between 18 and 75 years, female and male, skin phototype I-IV, no acute skin diseases on the exposed areas). The cream with *Echinacea* extract (0.5 wt %) and linoleic acid derivatives according to the invention and the body milk containing *Echinacea* extract (0.1 wt %) and linoleic acid derivatives according to the invention (corresponding to the example cream and example body milk described below) as well as the placebo of the cream with *Echinacea* extract and linoleic acid derivatives according to the invention were used as the test preparations.

Irritation/Induction Phase:

The products were applied to the same patch site continuously for 14 days occlusively with FinnChamber® Large (18 mm) on Fixomull® Stretch. Applications were made six times for 48 or 72 hours (150 µL per application). The test areas were located on the lower back. The erythema was evaluated visually using a scale from 0-6, 10-30 minutes after removal of the patch (Days 3, 5, 8, 10, 12, 15).

Challenge Phase (One Week Recuperation Following the Induction Phase):

The products were applied occlusively with FinnChamber® Large (18 mm) on Fixomull® Stretch. One application was made for 48 hours (150 µL per application). The test areas were located on the upper arm. The erythema was evaluated visually using a scale from 0-6, 10-30 minutes and 48 hours after removal of the patch.

Statistical Methods:

Irritation potential: The Cumulative Irritation Score for each subject was calculated as the total of the scores during the Irritation phase. The value from the preceding evaluation was used for any missing values. If a degree of 2 or more was recorded, the value of the second degree was transferred. A descriptive statistic (Average, Standard deviation, Minimum, Maximum and Median) was compiled for the Cumulative Irritation Score.

Sensitisation Potential:

The following categories of sensitisation potential were used:

Low: No subject reacts with a second degree or higher, or up to two subjects react with first degree to both evaluation points during the sensitisation phase.

Moderate: Up to two subjects react with a second degree or higher, or up to four subjects react with a first degree to both to both evaluation points during the sensitisation phase.

High: More than two subjects react with a second degree or higher, or more than four subjects react with first degree to both evaluation points during the sensitisation phase.

C) Irritation and Sensitisation Potential

A low to moderate irritation potential was found for all products tested. In this context, there were no statistically significant differences between the groups. A 48-hour occlusive application of the test product during the challenge phase did not result in the formation of first degree erythemas or higher on Days 24 and 26. According to the protocol, all products were categorised as having low sensitisation potential.

In view of the repeated occlusive applications for 48 hours without interruption between the applications, the absence of or low levels of irritation after the first application and the low levels of additional clinical signs of irritation, the skin tolerability of all products was categorised as good to very good. The sensitisation potential was classified as low with undetectable allergenic potential.

Example 7

Clinical SDS Irritation Study
A) Study Design
The study was conducted as a blind study.
B) Performance of the Study The study was conducted with 44 female test subjects. All test subjects participated in the 24-hour occlusive treatment with SDS (sodium dodecyl sulphate). Nine test subjects were excluded after evaluation of the baseline due to insufficient or inconsistent SDS irritations. Three further test subjects were excluded before the baseline evaluation due to excessive SDS irritation. The 31 test subjects who participated in the study until its conclusion were between 24.9 and 65.6 years old. The creams with Echinacea extract (1 and 2 wt %) and linoleic acid derivatives according to the invention were used as test preparations. Comparisons were made with untreated skin and with skin that was irritated with SDS (non-irritated/untreated, irritation with SDS/untreated). The primary objective was to evaluate the cosmetic properties of both creams with Echinacea extract and linoleic acid derivatives according to the invention. The secondary objective was to determine the influence of the creams with Echinacea extract and linoleic acid derivatives according to the invention on the reduction of erythema.

The epidermal barrier on the test sites on the test subjects' forearms was damaged by occlusive application for 24 hours of a 2% SDS solution in FinnChamber® (18 mm). Transepidermal water loss (TEWL, DermaLab®) and hydration of the skin (Corneometer® MDD4) was measured 4 h, 48 h, 3 d and 6 d after the irritation with SDS. In addition, the erythema was assessed visually (categorisation by technical experts). The two creams with Echinacea extract and linoleic acid derivatives according to the invention were applied to two test sites at random. A further test site on the forearm remained untreated. A test site on the upper arm served as a control site (not irritated/untreated). The two creams with Echinacea extract and linoleic acid derivatives according to the invention (~2 µL/cm$^2$) were applied twice daily.

The measurements and visual evaluations were carried out at the following times:
before the treatment with product, 4 h after removal of the patch ($t_0$)
after the 4th product application, 48 h after removal of the patch ($t_1$)
after the 6th product application, 3 d after removal of the patch ($t_2$)
after the 12th product application, 5 d after removal of the patch ($t_3$)

C) Transepidermal Water Loss (TEWL)

The treatment with the cream containing Echinacea extract (1 wt %) and linoleic acid derivatives according to the invention resulted in a slight, insignificant reduction in TEWL compared with the untreated site at times $t_0$ and $t_1$. No major differences between the two groups were detected at times $t_2$ and $t_3$. Following treatment with the cream containing Echinacea extract (2 wt %) and linoleic acid derivatives according to the invention, the TEWL values were generally higher than in the case of untreated skin. Elevated TEWL is an indicator of reduced epidermal barrier function. The results are presented in Table 1.

TABLE 1

Transepidermal water loss (TEWL), original data in g/m$^2$h

| Measurement time | SDS irritated/ untreated | 1% cream | 2% cream |
| --- | --- | --- | --- |
| $t_0$ | 41.3 | 39.9 | 41.5 |
| $t_1$ | 30.7 | 28.6 | 32.0 |
| $t_2$ | 18.6 | 19.1 | 22.2 |
| $t_3$ | 10.9 | 11.5 | 13.1 |

D) Skin Hydration (Corneometer®)

The test sites that were treated with the creams with Echinacea extract and linoleic acid derivatives according to the invention exhibited statistically significantly increased values for skin hydration on the treated test sites compared with the SDS-irritated, untreated skin sites at $t_2$ and $t_3$. The values for hydration of the skin were also higher at $t_1$. The results are presented in Table 2.

TABLE 2

Skin hydration, original data [AU]

| Measurement time | SDS irritated/ untreated | 1% cream | 2% cream |
| --- | --- | --- | --- |
| $t_0$ | 35.6 | 35.1 | 33.0 |
| $t_1$ | 19.3 | 20.9 | 20.6 |
| $t_2$ | 11.9 | 15.9 | 14.9 |
| $t_3$ | 9.6 | 16.1 | 12.8 |

E) Visual Determination of Erythema

As expected, erythema was not observed on the non-irritated, untreated test sites. Consequently, the Erythema Scores were significantly higher on all irritated sites. No major difference was observed between the sites treated with the cream with Echinacea extract and linoleic acid derivatives according to the invention and the untreated sites irritated with SDS. However, it was found that at $t_3$ the score for the sites treated with the cream with Echinacea extract (1 wt %) and linoleic acid derivatives according to the invention was lower than for the untreated sites irritated with SDS. In contrast to this, a lower score for the sites treated with the cream with Echinacea extract (2 wt %) and linoleic acid derivatives according to the invention was only found at $t_0$. At all other measurement times, the Erythema Score was higher than for the untreated sites that were irritated with SDS (insignificant). The results are presented in Table 3.

TABLE 3

Visual evaluation of erythema, original data

| Measurement time | Not irritated/ untreated | SDS irritated/ untreated | 1% cream | 2% cream |
|---|---|---|---|---|
| $t_0$ | 0.00 | 1.69 | 1.69 | 1.61 |
| $t_1$ | 0.00 | 1.44 | 1.47 | 1.50 |
| $t_2$ | 0.00 | 1.19 | 1.21 | 1.29 |
| $t_3$ | 0.00 | 0.94 | 0.87 | 0.97 |

In summary, it was found that the creams with *Echinacea* extract (1 wt % and 2 wt %) and linoleic acid derivatives according to the invention have a positive influence on skin moisture. This advantage outweighs the slightly elevated irritation which was also observed when the *Echinacea* extract was used in higher concentrations.

Example 8

Stability of the Formulations

The cream with *Echinacea* extract (0.5 wt %) and linoleic acid derivatives and the body milk with *Echinacea* extract (0.1 wt %) and linoleic acid derivatives (corresponding to the example cream and example body milk described below) were subjected to a long-term stability test. For this, samples were placed in storage under differing conditions (25° C./60% RH, 30° C./65% RH and 40° C./75% RH). The result of the tests revealed that both formulations have a shelf life of at least two years at room temperature.

Surprisingly, it was demonstrated in the examples 3 to 5 presented above that the cream according to the invention and the body milk according to the invention containing *Echinacea* extract and linoleic acid derivatives have a positive influence on the epidermal barrier function of the skin.

The treatment led to a significant increase in the numbers of the skin's own lipids, which are essential for restoring and maintaining the epidermal barrier. In particular, the content of ceramide EOS was also increased, which is particularly important for the stability of the lipid bilayers in the stratum corneum because of the "nail function".

A reduction of transepidermal water loss (TEWL) and in increase in skin moisture were demonstrated macroscopically in the studies. Moreover, pruritus was reduced following treatment with the products according to the invention.

The examples listed above show that, surprisingly, not only skin hydration can be improved in test subjects without epidermal barrier damage, as described in Yotsawimonwat S, et al., *Im J Cosm Sci* 2010, 32, 340-346, but that the formulations according to the invention can also help to regenerate an epidermal barrier which is already impaired. It is particularly noteworthy in this context that the formulations according to the invention differ from the known formulations containing *Echinacea* in more than just the additional presence of linoleic acid/linoleic acid derivatives. The extracts of *Echinacea purpurea* used are also different. Yotsawimonwat et al. used an alcoholic extract from the aboveground parts of *Echinacea*, which has a high content of phenolic components with antioxidant effect. The alkylamide content in such extracts is very low. The formulations according to the invention preferably contain an extract from the *Echinacea* roots. This has preferably been obtained using supercritical $CO_2$, and thus contains a high proportion of lipophilic alkylamides and no phenols.

It was also surprisingly found that the formulations according to the invention are able to be stored for a period of more than two years. This is also the case when they are stored at room temperature. In contrast, the formulations described by Yotsawimonwat et al. could only be stored for a maximum of 7 months at a temperature of 4° C. after the addition of an antioxidant.

It was also surprising to the person skilled in the art that the composition according to the invention exhibits antipruritic effects.

Examples of Compositions/Formulations According to the Present Invention:

Cream with 2% *Echinacea purpurea* Radix $CO_2$ Extract:

| | |
|---|---|
| Arlacel 1690 | 1.600 kg |
| Hexyldecyl laurate | 2.000 kg |
| Beeswax | 0.375 kg |
| Orange peel wax | 0.450 kg |
| Decyl oleate | 1.200 kg |
| Oxynex LM | 0.030 kg |
| Zinc stearate | 0.375 kg |
| Safflower oil | 2.550 kg |
| Isopropyl myristate | 1.500 kg |
| *Echinacea purpurea* radix $CO_2$ extract | 0.600 kg |
| Benzyl alcohol | 0.300 kg |
| Magnesium sulphate heptahydrate | 0.150 kg |
| Glycerol | 0.900 kg |
| Water, purified | 17.970 kg |

Cream with 1% *Echinacea purpurea* Radix $CO_2$ Extract:

| | |
|---|---|
| Arlacel 1690 | 1.600 kg |
| Hexyldecyl laurate | 2.000 kg |
| Beeswax | 0.375 kg |
| Orange peel wax | 0.450 kg |
| Decyl oleate | 1.200 kg |
| Oxynex LM | 0.030 kg |
| Zinc stearate | 0.375 kg |
| Safflower oil | 2.550 kg |
| Isopropyl myristate | 1.500 kg |
| *Echinacea purpurea* radix $CO_2$ extract | 0.300 kg |
| Benzyl alcohol | 0.300 kg |
| Magnesium sulphate heptahydrate | 0.150 kg |
| Glycerol | 0.900 kg |
| Water, purified | 18.270 kg |

Cream with 0.5% *Echinacea purpurea* Radix $CO_2$ Extract:

| | |
|---|---|
| Arlacel 1690 | 1.600 kg |
| Hexyldecyl laurate | 2.000 kg |
| Beeswax | 0.375 kg |
| Orange peel wax | 0.450 kg |
| Decyl oleate | 1.200 kg |
| Oxynex LM | 0.030 kg |
| Zinc stearate | 0.375 kg |
| Safflower oil | 2.550 kg |
| Isopropyl myristate | 1.500 kg |
| *Echinacea purpurea* radix $CO_2$ extract | 0.150 kg |
| Benzyl alcohol | 0.300 kg |
| Magnesium sulphate heptahydrate | 0.150 kg |
| Glycerol | 0.900 kg |
| Water, purified | 18.420 kg |

Body Milk with 0.1% *Echinacea purpurea* Radix $CO_2$ Extract:

| | |
|---|---|
| Zinc stearate | 0.300 kg |
| Orange peel wax | 0.200 kg |
| Arlacel 1690 | 1.500 kg |
| Hexyldecyl laurate | 2.500 kg |
| Safflower oil | 2.550 kg |

-continued

| | |
|---|---|
| Decyl oleate | 1.500 kg |
| Isopropyl myristate | 1.200 kg |
| Benzyl alcohol | 0.300 kg |
| Oxynex LM | 0.030 kg |
| *Echinacea purpurea* radix $CO_2$ extract | 0.030 kg |
| Magnesium sulphate heptahydrate | 0.150 kg |
| Glycerol | 0.900 kg |
| Water, purified | 18.840 kg |

Body Milk with 0.02% *Echinacea purpurea* Radix $CO_2$ Extract:

| | |
|---|---|
| Zinc stearate | 0.300 kg |
| Orange peel wax | 0.200 kg |
| Arlacel 1690 | 1.500 kg |
| Hexyldecyl laurate | 2.500 kg |
| Safflower oil | 2.550 kg |
| Decyl oleate | 1.500 kg |
| Isopropyl myristate | 1.200 kg |
| Benzyl alcohol | 0.300 kg |
| Oxynex LM | 0.030 kg |
| *Echinacea purpurea* radix $CO_2$ extract | 0.006 kg |
| Magnesium sulphate heptahydrate | 0.150 kg |
| Glycerol | 0.900 kg |
| Water, purified | 18.864 kg |

The invention claimed is:

1. Composition containing a) an extract of *Echinacea* and b) linoleic acid and/or linoleic acid derivatives, wherein the linoleic acid and/or linoleic acid derivatives are not part of the extract of *Echinacea*, wherein the extract of *Echinacea* is a $CO_2$ extract, wherein the composition contains the components a) and b) in the following weight proportions: 1:1000 to 1:1.

2. Composition according to claim 1, characterized in that the extract of *Echinacea* is a lipophilic extract.

3. Composition according to claim 1, characterized in that the extract of *Echinacea* has an alkylamide content between 1 and 50%.

4. Composition according to claim 1, characterized in that the extract of *Echinacea* originates from the roots of *Echinacea*.

5. Composition according to claim 1, characterized in that the linoleic acid derivatives are linoleic acid esters.

6. Composition according to claim 1, characterized in that the linoleic acid derivatives are present in the form of a vegetable oil and/or vegetable oil extract.

7. Composition according to claim 1, further comprising one or more cosmetic and/or pharmaceutical adjuvants.

8. Composition according to claim 3, characterized in that the extract of *Echinacea* has an alkylamide content between 10% and 40%.

9. Composition according to claim 8, characterized in that the extract of *Echinacea* has an alkylamide content between 15% and 30%.

10. Composition according to claim 4, characterized in that the extract of *Echinacea* originates from *Echinacea purpurea radix*.

11. Composition according to claim 5, characterized in that the linoleic acid derivatives are glycerol triesters.

12. Composition according to claim 6, characterized in that the linoleic acid derivatives are present in the form of a safflower oil and/or safflower oil extract.

13. Composition according to claim 1, wherein the composition contains no other plant extracts.

14. Composition containing a) an extract of *Echinacea* and b) linoleic acid and/or linoleic acid derivatives, wherein the linoleic acid and/or linoleic acid derivatives are not part of the extract of *Echinacea*, wherein the extract of *Echinacea* is a $CO_2$ extract, wherein 0.001-5 wt % *Echinacea* extract, and 0.001-10 wt % linoleic acid and/or a similar quantity of linoleic acid derivatives corresponding to 0.001-10 wt % linoleic acid, are contained, relative to the total weight of the composition in each case, wherein the linoleic acid and/or linoleic acid derivative is chosen from the group consisting of salicornia oil, evening primrose oil, grape seed oil, safflower oil, poppy seed oil, prickly pear seed oil, hemp oil, soya oil, cottonseed oil, wheatgerm oil, corn oil, sunflower oil, walnut oil, sesame oil, argan oil, pistachio oil, peanut oil, rapeseed oil, rice oil and olive oil.

15. Composition according to claim 14, characterized in that 0.025-2 wt % *Echinacea* extract relative to the weight of the total composition, 0.01-5 wt % linoleic acid and/or a similar quantity of linoleic acid derivatives corresponding to 0.01-5 wt % linoleic acid relative to the total weight of the composition in each case.

16. Composition according to claim 14, characterized in that the extract of *Echinacea* is a lipophilic extract.

17. Composition according to claim 14, wherein the extract of *Echinacea* has an alkylamide content between 1 and 50%.

18. Composition according to claim 14, further comprising one or more cosmetic and/or pharmaceutical adjuvants.

19. Composition according to claim 14, characterized in that the extract of *Echinacea* originates from the roots of *Echinacea*.

20. Composition according to claim 19, characterized in that the extract of *Echinacea* originates from *Echinacea purpurea radix*, wherein the composition contains no other plant extracts.

* * * * *